United States Patent
Knopp

(10) Patent No.: US 7,357,634 B2
(45) Date of Patent: Apr. 15, 2008

(54) SYSTEMS AND METHODS FOR SUBSTITUTING VIRTUAL DENTAL APPLIANCES

(75) Inventor: Peter G. Knopp, Palo Alto, CA (US)

(73) Assignee: Align Technology, Inc., Santa Clara, CA (US)

( * ) Notice: Subject to any disclaimer, the term of this patent is extended or adjusted under 35 U.S.C. 154(b) by 80 days.

(21) Appl. No.: 10/981,855

(22) Filed: Nov. 5, 2004

(65) Prior Publication Data

US 2006/0099547 A1 May 11, 2006

(51) Int. Cl.
*A61C 3/00* (2006.01)
(52) U.S. Cl. .......................... 433/24; 433/6
(58) Field of Classification Search ............. 433/24, 433/6
See application file for complete search history.

(56) References Cited

U.S. PATENT DOCUMENTS

| | | | |
|---|---|---|---|
| 2,467,432 A | 4/1949 | Kesling | |
| 3,660,900 A | 5/1972 | Andrews | |
| 3,860,803 A | 1/1975 | Levine | |
| 3,916,526 A | 11/1975 | Schudy | |
| 3,950,851 A | 4/1976 | Bergersen | |
| 4,014,096 A | 3/1977 | Dellinger | |
| 4,195,046 A | 3/1980 | Kesling | |
| 4,324,546 A | 4/1982 | Heitlinger et al. | |
| 4,348,178 A | 9/1982 | Kurz | |
| 4,478,580 A | 10/1984 | Barrut | |
| 4,504,225 A | 3/1985 | Yoshii | |
| 4,505,673 A | 3/1985 | Yoshii | |
| 4,575,805 A | 3/1986 | Moermann et al. | |
| 4,611,288 A | 9/1986 | Duret et al. | |
| 4,656,860 A | 4/1987 | Orthuber et al. | |
| 4,663,720 A | 5/1987 | Duret et al. | |
| 4,742,464 A | 5/1988 | Duret et al. | |
| 4,755,139 A | 7/1988 | Abbatte et al. | |
| 4,763,791 A | 8/1988 | Halverson et al. | |
| 4,793,803 A | 12/1988 | Martz | |
| 4,798,534 A | 1/1989 | Breads | |
| 4,837,732 A | 6/1989 | Brandestini et al. | |
| 4,850,864 A | 7/1989 | Diamond | |
| 4,856,991 A | 8/1989 | Breads et al. | |
| 4,936,862 A | 6/1990 | Walker et al. | |
| 4,937,928 A | 7/1990 | Van Der Zel | |

(Continued)

FOREIGN PATENT DOCUMENTS

EP      0091876 A1    10/1983

(Continued)

OTHER PUBLICATIONS

Alexander et al., "The DigiGraph Work Station Part 2, Clinical Management," *JCO* (Jul. 1990), pp. 402-407.

(Continued)

*Primary Examiner*—Cris Rodriguez
*Assistant Examiner*—Candice C. Stokes
(74) *Attorney, Agent, or Firm*—Brooks, Cameron & Huebsch, PLLC

(57) ABSTRACT

Systems and methods are disclosed for performing virtual treatment using one or more dental appliances by receiving a digital model of a dental appliance; selecting a standard position and orientation; and mapping the digital model of the dental appliance to the standard position and orientation.

23 Claims, 4 Drawing Sheets

RECEIVE A DIGITAL MODEL OF A DENTAL APPLIANCE
110

SELECT A STANDARD POSITION AND ORIENTATION
120

MAP THE DIGITAL MODEL OF THE DENTAL APPLIANCE TO THE STANDARD POSITION AND ORIENTATION
130

U.S. PATENT DOCUMENTS

| | | | |
|---|---|---|---|
| 4,964,770 | A | 10/1990 | Steinbichler et al. |
| 4,975,052 | A | 12/1990 | Spencer et al. |
| 5,011,405 | A | 4/1991 | Lemchen |
| 5,017,133 | A | 5/1991 | Miura |
| 5,027,281 | A | 6/1991 | Rekow et al. |
| 5,035,613 | A | 7/1991 | Breads et al. |
| 5,055,039 | A | 10/1991 | Abbatte et al. |
| 5,059,118 | A | 10/1991 | Breads et al. |
| 5,100,316 | A | 3/1992 | Wildman |
| 5,121,333 | A | 6/1992 | Riley et al. |
| 5,128,870 | A | 7/1992 | Erdman et al. |
| 5,131,843 | A | 7/1992 | Hilgers et al. |
| 5,131,844 | A | 7/1992 | Marinaccio et al. |
| 5,139,419 | A | 8/1992 | Andreiko et al. |
| 5,184,306 | A | 2/1993 | Erdman et al. |
| 5,186,623 | A | 2/1993 | Breads et al. |
| 5,257,203 | A | 10/1993 | Riley et al. |
| 5,273,429 | A | 12/1993 | Rekow et al. |
| 5,278,756 | A | 1/1994 | Lemchen et al. |
| 5,338,198 | A | 8/1994 | Wu et al. |
| 5,340,309 | A | 8/1994 | Robertson |
| 5,342,202 | A | 8/1994 | Deshayes |
| 5,368,478 | A | 11/1994 | Andreiko et al. |
| 5,382,164 | A | 1/1995 | Stern |
| 5,395,238 | A | 3/1995 | Andreiko et al. |
| 5,431,562 | A | 7/1995 | Andreiko et al. |
| 5,440,326 | A | 8/1995 | Quinn |
| 5,440,496 | A | 8/1995 | Andersson et al. |
| 5,447,432 | A | 9/1995 | Andreiko et al. |
| 5,452,219 | A | 9/1995 | Dehoff et al. |
| 5,454,717 | A | 10/1995 | Andreiko et al. |
| 5,456,600 | A | 10/1995 | Andreiko et al. |
| 5,474,448 | A | 12/1995 | Andreiko et al. |
| 5,518,397 | A | 5/1996 | Andreiko et al. |
| 5,533,895 | A | 7/1996 | Andreiko et al. |
| 5,542,842 | A | 8/1996 | Andreiko et al. |
| 5,549,476 | A | 8/1996 | Stern |
| 5,587,912 | A | 12/1996 | Andersson et al. |
| 5,605,459 | A | 2/1997 | Kuroda et al. |
| 5,607,305 | A | 3/1997 | Andersson et al. |
| 5,645,421 | A | 7/1997 | Slootsky |
| 5,655,653 | A | 8/1997 | Chester |
| 5,683,243 | A | 11/1997 | Andreiko et al. |
| 5,733,126 | A | 3/1998 | Andersson et al. |
| 5,740,267 | A | 4/1998 | Echerer et al. |
| 5,975,893 | A | 11/1999 | Chishti et al. |
| 6,409,504 | B1 * | 6/2002 | Jones et al. .................. 433/24 |
| 6,471,511 | B1 * | 10/2002 | Chishti et al. ................ 433/24 |
| 2006/0093992 | A1 * | 5/2006 | Wen ........................... 433/213 |

FOREIGN PATENT DOCUMENTS

| | | |
|---|---|---|
| EP | 0376873 A2 | 7/1990 |
| EP | 0490848 A2 | 6/1992 |
| EP | 0774933 B1 | 5/1997 |
| EP | 0541500 A1 | 6/1998 |
| EP | 0731673 B1 | 9/1998 |
| FR | 2652256 A1 | 3/1991 |
| WO | WO 90/08512 A1 | 8/1990 |
| WO | WO 91/04713 A1 | 4/1991 |
| WO | WO 94/10935 A1 | 5/1994 |
| WO | WO 98/44865 A1 | 10/1998 |
| WO | WO 98/58596 A1 | 12/1998 |

OTHER PUBLICATIONS

Altschuler et al, "Measuring Surfaces Space-Coded by a Laser-Projected Dot Matrix," *SPIE Imaging Applications for Automated Industrial Inspection and Assembly*, vol. 182 (1979), p. 187-191.

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, *Journal of Dental Research*, vol. 58, Jan. 1979, Special Issue A, p. 221.

Altschuler et al., "Laser Electro-Optic System for Rapid Three-Dimensional (3D) Topographic Mapping of Surfaces," *Optical Engineering*, vol. 20(6) (1981), pp. 953-961.

Altschuler, "3D Mapping of Maxillo-Facial Prosthesis," AADR Abstract #607, 1980, 1 page total.

American Association for Dental Research, Summary of Activities, Mar. 20-23, 1980, Los Angeles, CA, p. 195.

Andersson et al., "Clinical Results with Titanium Crowns Fabricated with Machine Duplication and Spark Erosion," *Acta Odontological Scandinavia*, vol. 47 (1989), pp. 279-286.

Baumrind et al., "A Stereophotogrammetric System for the Detection of Prosthesis Loosening in Total Hip Arthroplasty", NATO Symposium on Applications of Human Biostereometrics, Jul. 9-13, 1978, SPIE vol. 166, pp. 112-123.

Baumrind et al., Mapping the Skull in 3-D, Reprinted from The Journal, *California Dental Association*, vol. 48, No. 2 (1972 Fall Issue) 11 pages total.

Baumrind, "A System for Craniofacial Mapping Through the Integration of Data from Stereo X-Ray Films and Stereo Photographs," An invited paper submitted to the 1975 American Society of Photogram. Symposium on Close-Range Photogram. Systems, University of Ill., Aug. 26-30, 1975, pp. 142-166.

Baumrind, "Integrated Three-Dimensional Craniofacial Mapping: Background, Principles, and Perspectives," *Seminars in Orthodontics*, vol. 7, No. 4 (Dec. 2001), pp. 223-232.

Begole et al., "A Computer System for the Analysis of Dental Casts," *The Angle Orthodontist*, vol. 51 No. 3 (Jul. 1981), pp. 253-259.

Bernard et al., "Computerized Diagnosis in Orthodontics for Epidemiological Studies: A Progress Report", Abstracts of Papers, *Journal of Dental Research*; vol. 67, Special Issue Mar. 9-13, 1988, p. 169.

Bhatia et al., "A Computer-Aided Design for Orthognathic Surgery," *British Journal of Oral and Maxillofacial Surgery*, vol. 22 (1984), pp. 237-253.

Biggerstaff et al., "Computerized Analysis of Occlusion In The Postcanine Dentition," *American Journal of Orthodontics*, vol. 61, No. 3 (Mar. 1972), pp. 245-254.

Biggerstaff, "Computerized Diagnostic Setups and Simulations," *The Angle Orthodontist*, vol. 40, No. 1 (Jan. 1970), pp. 28-36.

Boyd et al., "Three Dimensional Diagnosis and Orthodontic Treatment of Complex Malocclusions Wlith the Invisalign Appliance", *Seminars in Orthodontics*, vol. 7, No. 4 (Dec. 2001), p. 274-293.

Brandestini et al., "Computer Machined Ceramic Inlays: In Vitro Marginal Adaptation," *Journal of Dental Research*, vol. 64/Special Issue/Abstracts, IADR/AADR Abstracts 1985, p. 208.

Brook et al., An Image Analysis System for the Determination of Tooth Dimensions from Study Casts: Comparison with Manual Measurements of Mesio-distal Diameter, *J Dent Res.*, vol. 65, No. 3, Mar. 1986, pp. 428-431.

Burstone (interview), "Dr. Charles J. Burstone on The Uses of the Computer in Orthodontic Practice (Parts 1 and 2)," *Journal of Clinical Orthodontics*, (Part 1) vol. 8, No. 7, Jul. 1979; (Part 2) vol. 8, No. 8 pp. 539-551, Aug. 1979.

Burstone et al., "Precision Adjustment of the Transpalatal Lingual Arch: Computer Arch Form Predetermination," *Am. Journal of Orthodontics*, vol. 79, No. 2 (Feb. 1981), pp. 115-133.

Chaconas et al., "The DigiGraph Work Station, Part 1, Basic Concepts," *JCO* (Jun. 1990), pp. 360-367.

Chafetz et al., "Subsidence of the Femoral Prosthesis, A Stereophotogrammetric Evaluation," *Clinical Orthopaedics and Related Research*, No. 201 (Dec. 1985), pp. 60-67.

Chiappone, "Constructing the Gnathologic Setup And Positioner" *J. Clin. Orthod.*, 14:121-133, 1980.

Cottingham, "Gnathologic Clear Plastic Positioner" *Am. J. Orthod.*, vol. 55, No. 1, (Jan. 1969),. pp. 23-31.

Crawford, "Computers in Dentistry: Part 1: CAD/CAM: The Computer Moves Chairside," "Part 2: F. Duret—A Man With A Vision," "Part 3: The Computer Gives New Vision—Literally," "Part 4:

Bytes 'N Bites" The Computer Moves From The Front Desk To The Operatory, *Canadian Dental Journal*, vol. 54(9), , (1988), pp. 661-666.

Crawford, "CAD/CAM in the Dental Office: Does It Work?" *Canadian Dental Journal*, vol. 57, No. 2 (Feb. 1991), pp. 121-123.

Crooks, "CAD/CAM Comes to USC," *USC Dentistry*, (Spring 1990) pp. 14-17.

Cureton, "Correcting Malaligned Mandibular Incisors With Removable Retainers" *J. Clin. Orthod.*, 30:390-395, 1996.

Curry et al., "Integrated Three-Dimensional Craniofacial Mapping at the Craniofacial Research Instrumentation Laboratory/University of the Pacific," *Seminars in Orthodontics*, vol. 7, No. 4 (Dec. 2001), pp. 258-265.

Cutting et al., "Three-Dimensional Computer-Assisted Design of Craniofacial Surgical Procedures: Optimization and Interaction with Cephalometric and CT-Based Models," *Plastic and Reconstructive Surgery*, vol. 77, No. 6 (Jun. 1986), pp. 877-885.

Heaven et al., "Computer-based Image Analysis of Artificial Root Surface Caries," Abstracts of Papers, *Journal of Dental Research*, vol. 70,Apr. 17-21, 1991, p. 528.

Hoffmann et al., "Role of Cephalometry for Planning of Jaw Orthopedics and Jaw Surgery Procedures," (Article Summary in English, article in German), *Informationen*, (Mar. 1991), pp. 375-396.

Huckins, "CAD-CAM Generated Mandibular Model Prototype from MRI Data," *AAOMS* 1999, p. 96.

JCO Interviews, "Craig Andreiko, DDS, MS on the Elan and Orthos Systems", JCO, (Aug. 1994), pp. 459-468.

JCO Interviews, "Dr. Homer W. Phillips on Computers in Orthodontic Practice, Part 2," JCO, (Dec. 1983), pp. 819-831.

Jerrold, "The Problem, Electronic Data Transmission and the Law," *AJO-DO*, (Apr. 1988), pp. 478-479.

Jones et al., "An Assessment of the Fit of a Parabolic Curve to Pre- and Post-Treatment Dental Arches," *British Journal of Orthodontics*, vol. 16 (1989), pp. 85-93.

Kamada et al., "Case Reports on Tooth Positioners Using LTV Vinyl Silicone Rubber" J. Nihon University School of Dentistry, 26(1):11-29, 1984.

Kamada et al., "Construction of Tooth Positioners With LTV Vinyl Silicone Rubber and Some Case Reports" J. Nihon University School of Dentistry, 24(1):1-27, 1982.

Kanazawa et al., "Three-Dimensional Measurements of the Occlusal Surfaces of Upper Molars In a Dutch Population," *J. Dent Res.* , vol. 63, No. 11 (Nov. 1984), pp. 1298-1301.

Kesling, "Coordinating the Predetermined Pattern and Tooth Positioner With Conventional Treatment" *Am. J. Orthod. Oral. Surg.*, 32:285-293, 1946.

Kesling, "The Philosophy of the Tooth Positioning Appliance" *Am. J. Orthod. Oral. Surg.*, 31(6):297-304, 1945.

Kleemann et al., "The Speed Positioner" *J. Clin. Orthod.*, 30:673-680, 1996.

Kuroda et al., "Three-dimensional dental cast analyzing system using laser scanning" *Am. J. Orthod. Dentofac. Orthop.*, 110:365-369, 1996.

Laurendeau et al., "A Computer-Vision Technique for the Acquisition and Processing of 3-D Profiles of Dental Imprints: An Application in Orthodontics," *IEEE Transactions on Medical Imaging*, vol. 10, No. 3 (Sep. 1991), pp. 453-461.

Manetti et al., "Computer-aided Cefalometry and New Mechanics in Orthodontics" (Article Summary in English, article in German), *Fortschr. Kieferothop.* 44, 370-376 (Nr. 5), 1983.

McCann, Inside the ADA, *Journal Of The American Dental Assoc.*, vol. 118 (Mar. 1989) pp. 286-294.

McNamara et al., "Invisible Retainers", *J. Clinical Orthodontics*, (Aug. 1985) pp. 570-578.

McNamara et al., Chapter 19: Invisible Retainers, *Orthodontic and Orthopedic Treatment in the Mixed Dentition*, Needham Press, Jan. 1993. pp. 347-353.

Moermann et al., "Computer Machined Adhesive Porcelain Inlays: Margin Adaptation after Fatigue Stress," IADR Abstract 339, *Journal of Dental Research*, vol. 66(a) (1987), p. 763.

Mörmann et al., "Marginal Adaptation von adhasiven Porzellaninlays in vitro," *Schwizerische Monatsshrift fur Zahnmedizin*, vol. 85 (1985), p. 1118-1129.

Nahoum, "The Vacuum Formed Dental Contour Appliance" *The New York State Dental Journal*, 30(9):385-390, Nov. 1964.

Nash, "CEREC CAD/CAM Inlays: Aesthetics and Durability in a Single Appointment," *Dentistry Today*, (Oct. 1990), pp. 20, 22-23, 54.

Nishiyama et al., "A New Construction Of Tooth Repositioner By LTV Vinyl Silicone Rubber" J. Nihon University School of Dentistry, 19(2):93-102, 1977.

Pinkham, "Foolish' Concept Propels Technology," *Dentist*, Jan./Feb. 1989, 3 pages total.

Pinkham, "Inventor's CAD/CAM May Transform Dentistry," *Dentist*, Sep. 1990, 3 pages total.

Ponitz, "Invisible Retainers", *Am. J. Orthodontics*, vol. 59, No. 3, Mar. 1971, pp. 266-272.

Procera Research Projects, *PROCERA Research Projects* 1993—Abstract Collection, 1993, pp. 3-24.

Rekow, "A Review of the Developments in Dental CAD/CAM Systems," (contains references to Japanese efforts and content of the papers of particular interest to the clinician are indicated with a one-line summary of their content in the bibliography), Dental Clinics: *Prosthodontics and Endodontics*, pp. 25-33, 1992.

Rekow, "CAD/CAM in Dentistry: A Historical Perspective and View of the Future," *Journal*, vol. 58 No. 4, (Apr. 1992), pp. 283, 287-288.

Rekow, "Computer-Aided Design and Manufacturing in Dentistry: A Review of the State of the Art," *The Journal of Prosthetic Dentistry*, vol. 58, No. 4 (Oct. 1987), pp. 512-516.

Van Der Zel, "Ceramic-fused-to-metal Restorations with a New CAD/CAM System," *Quintessence International*, vol. 24(11) (1993), pp. 769-778.

Varady et al., Reverse Engineering Of Geometric Models—An Introduction. Computer-Aided Design, 29 (4):255-268, 1997.

Warunek et al., "Clinical Use Of Silicone Elastomer Appliances" *JCO*, MH (10):694-700, 1989.

Warunek et al., "Physical And Mechanical Properties of Elastomers In Orthodontic Positioners" *Am. J. Orthod. Dentofac. Orthop.*, 95:388-400, 1989.

Wells, "Application of the Positioner Appliance in Orthodontic Treatment" *Am. J. Orthodont.*, 58:351-366, 1970.

Williams, "Dentistry and CAD/CAM: Another French Revolution," *Journal of Dental Practice Admin.*, Jan./Mar. 1987, pp. 2-5.

Williams, "The Switzerland and Minnesota Developments in CAD/CAM," *Journal of Dental Practice Admin.*, pp. 50-55, Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5.

Yamamoto et al., "Three-Dimensional Measurement of Dental Cast Profiles and Its Applications to Orthodontics," Annual Int'l Conf. of IEEE Engineering in Medicine and Biology Society, vol. 12, No. 5, pp. 2051-2053, 1990.

Yamamoto et al., "Optical Measurement of Dental Cast Profile and Application to Analysis of Three-Dimensional Tooth Movement in Orthodontics," *Frontiers in Med. and Biol. Eng'g*, vol. 1, No. 2 (1988), pp. 119-130.

ISA/US, International Search Report and Written Opinion for International Application No. PCT/US05/39475, 9 pages, Jul. 11, 2006.

Rekow, "Dental CAD-CAM Systems: What is the State of the Art?" *Journal of the American Dental Assoc.*, vol. 122 (1991), pp. 43-48.

Rekow, "Feasibility of an Automated System for Production of Dental Restorations;" PhD Thesis, Univ. of Minnesota, Nov. 1988, 244 pages total.

Richmond et al., Research Reports, "The Development of a 3D Cast Analysis System," *British Journal of Orthodontics*, vol. 13, No. 1, (Jan. 1986) pp. 53-54.

Richmond, "Recording The Dental Cast In Three Dimensions," *Am. J. Orthod. Dentofac. Orthop.*, vol. 92, No. 3, (Sep. 1987), pp. 199-206.

Rudge, "Dental arch analysis: Arch Form, A review of the literature," *European Journal of Orthodontics*, vol. 3, No. 4 (1981), pp. 279-284.

Sakuda et al., "Integrated information-processing system in clinical orthodontics: An approach with use of a computer network system," *Am. J. Orthod. Dentofac. Orthop.* vol. 101 No. 3 (Mar. 1992), pp. 210-220.

Schellhas et al., "Three-Dimensional Computed Tomography in Maxillofacial Surgical Planning," *Arch Otolamgol Head Neck Surg.* vol. 114 (Apr. 1988), pp. 438-442.

Shilliday, "Minimizing Finishing Problems With the Mini-Positioner" *Am. J. Orthod.* 59:596-599, 1971.

Sirona Dental Systems GmbH, CEREC 3D, Manuel utilisateur, Version 2.0X (in French), 2003, 114 pages total.

Stoll et al., "Computer-aided Technologies in Dentistry" (Article Summary in English, article in German), *Dtsch Zahnärztl Z* 45, 314-322, 1990.

U.S. Department of Commerce, National Technical Information Service, "Automated Crown Replication Using Solid Photography SM," Solid Photography Inc. Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed Jun. 20, 1997, 41 pages total.

Van Der Linden et al., "Three-Dimensional Analysis of Dental Casts by Means of the Optocom," *J Dent Res*, Jul.-Aug. 1972, vol. 51, No. 4, p. 1101.

Van Der Linden, "A New Method to Determine Tooth Positions and Dental Arch Dimensions," Jul.-Aug. 1972, p. 1104.

DCS Dental AG, "The CAD/CAM 'DCS Titan System' for Production of Crowns/Bridges" *DSC Production AG*, Jan. 1992, pp. 1-7.

Defranco et al., "Three-Dimensional Large Displacement Analysis of Orthodontic Appliances," *J. Biomechanics*, vol. 9 (1976), pp. 793-801.

Dental Institute University of Zurich Switzerland, Program for International Symposium on Computer Restorations: State of the Art of the CEREC-Method, May 1991, 2 pages total.

Duret et al, "CAD-CAM in Dentistry," *Journal of the American Dental Association*, vol. 117 (Nov. 1988), pp. 715-720.

Duret et al., "CAD/CAM Imaging in Dentistry," *Current Opinion in Dentistry*, vol. 1 (1991), pp. 150-154.

Duret, "Vers une prosthese informatisee," (English translation also attached), *Tonus*, vol. 75, (Nov. 15, 1985), pp. 55-57.

Duret, "The Dental CAD/CAM, General Description of the Project," *Hennson International Product Brochure*, Jan. 1986., 18 pages total.

Economides, "The Microcomputer in the Orthodontic Office," *JCO*, (Nov. 1979), pp. 767-772.

Elsasser, "Some Observations on the History and Uses of the Kesling Positioner" *Am. J. Orthod.*, vol. 36, No. 5, (May 1950) pp. 368-374.

Faber et al., "Computerized interactive orthodontic treatment planning," *Am. J. Orthod.*, vol. 73, No. 1 (Jan. 1978), pp. 36-46.

Felton et al. "A computerized analysis of the shape and stability of mandibular arch form," *Am. Journal of Orthodontics and Dentofacial Orthopedics*, vol. 92, No. 6 (Dec. 1987), pp. 478-483.

Friede et al., "Accuracy of Cephalometric Prediction in Orthognathic Surgery," Abstract of Papers, *Journal of Dental Research*, vol. 70 (1987), pp. 754-760.

Grayson, "New Methods for Three Dimensional Analysis of Craniofacial Deformity," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5-6.

Guess et al., "Computer Treatment Estimates in Orthodontics and Orthognathic Surgery," *JCO*, (Apr. 1989), pp. 262-268.

\* cited by examiner

```
┌─────────────────────────────────────────────────┐
│   RECEIVE A DIGITAL MODEL OF A DENTAL APPLIANCE │
│                       110                       │
├─────────────────────────────────────────────────┤
│   SELECT A STANDARD POSITION AND ORIENTATION    │
│                       120                       │
├─────────────────────────────────────────────────┤
│   MAP THE DIGITAL MODEL OF THE DENTAL APPLIANCE │
│      TO THE STANDARD POSITION AND ORIENTATION   │
│                       130                       │
└─────────────────────────────────────────────────┘
```

FIG. 1A

```
┌─────────────────────────────────────────────────┐
│   SELECT A MODEL OF A DENTAL APPLIANCE PLACED   │
│                 ON A TOOTH MODEL                │
│                       150                       │
├─────────────────────────────────────────────────┤
│      SELECT A MODEL OF A SUBSTITUTE DENTAL      │
│                    APPLIANCE                    │
│                       160                       │
├─────────────────────────────────────────────────┤
│   PLACE THE SUBSTITUTE MODEL IN PLACE OF THE    │
│  ORIGINAL MODEL OF THE DENTAL APPLIANCE BASED   │
│     ON THE STANDARD POSITION AND ORIENTATION    │
│                       170                       │
└─────────────────────────────────────────────────┘
```

FIG. 1B

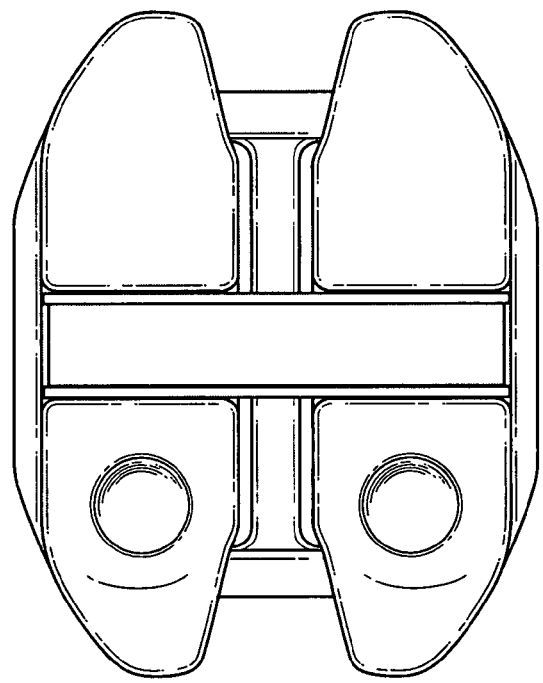
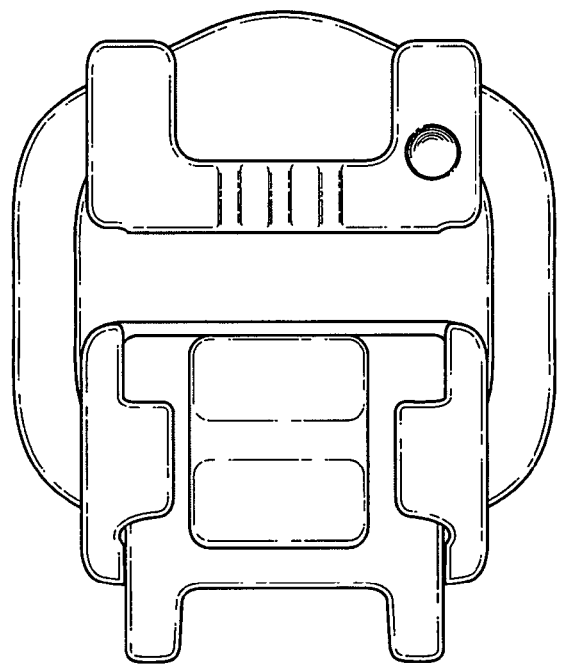
FIG. 2

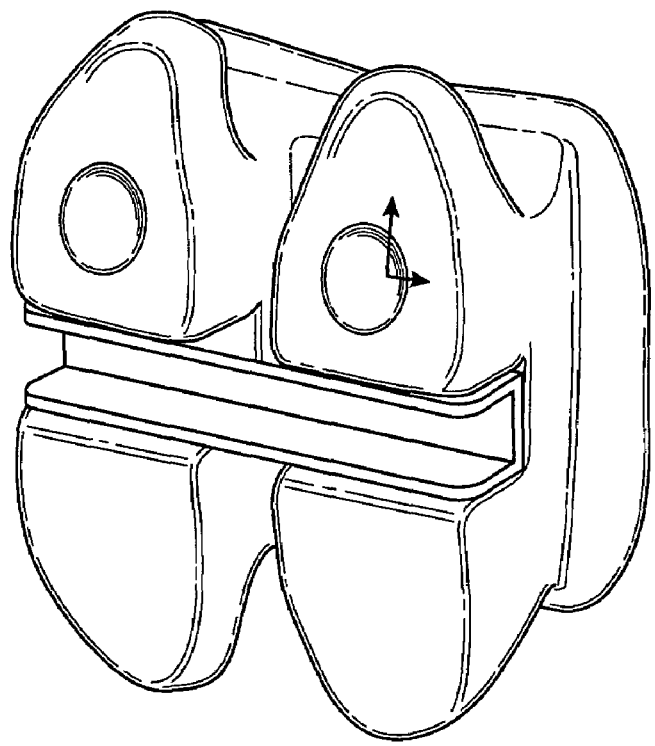
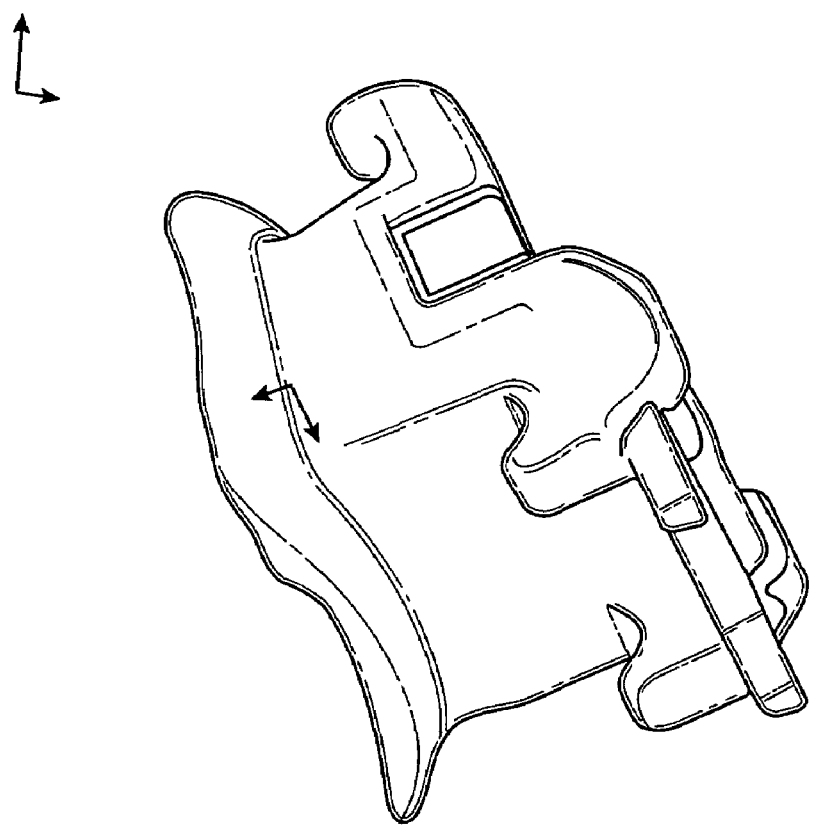
FIG. 3

SYSTEMS AND METHODS FOR SUBSTITUTING VIRTUAL DENTAL APPLIANCES

BACKGROUND

The invention relates generally to computer-automated development of an orthodontic treatment and appliance.

Orthodontics is the branch of dentistry that deals with the straightening of crooked teeth. Although there are many types of appliances that can be used by an orthodontist to straighten the teeth, the most common appliance is braces. Braces include a variety of appliances such as brackets, archwires, ligatures, and O-rings, and attaching braces to a patient's teeth is a tedious and time consuming enterprise requiring many meetings with the treating orthodontist. Consequently, conventional orthodontic treatment limits an orthodontist's patient capacity and makes orthodontic treatment quite expensive.

Before fastening braces to a patient's teeth, at least one appointment is typically scheduled with the orthodontist, dentist, and/or X-ray laboratory so that X-rays and photographs of the patient's teeth and jaw structure can be taken. Also during this preliminary meeting, or possibly at a later meeting, an alginate mold of the patient's teeth is typically made. This mold provides a model of the patient's teeth that the orthodontist uses in conjunction with the X-rays and photographs to formulate a treatment strategy. The orthodontist then typically schedules one or more appointments during which braces will be attached to the patient's teeth.

Historically, the practice of orthodontics has been a manual process that relied on the doctor's skills and judgment. A number of parties are creating and providing products and services that can be grouped together under the appellation 'virtual orthodontics'. The principle elements of virtual orthodontics are representations of the teeth and of orthodontic components such as brackets and wire.

One of the values of virtual orthodontics is that the user can make choices among available components before actually implementing the treatment approach. For instance, an orthodontist can evaluate options by choosing different bracket prescriptions and features such as hooks or ligation methods before the brackets are applied to a patient's teeth.

SUMMARY

Systems and methods are disclosed for performing virtual treatment using one or more dental appliances by receiving a digital model of a dental appliance; selecting a standard position and orientation; and mapping the digital model of the dental appliance to the standard position and orientation.

Advantages may include one or more of the following. The system allows the doctors to easily change or substitute different brackets during treatment planning. Thus, the doctor can simply select a different bracket and the system automatically places the new bracket in the proper position and orientation relative to its underlying tooth. This is achieved by having all brackets in the same spatial coordinate system or making use of a transform function to relate the coordinate systems of the brackets.

BRIEF DESCRIPTION OF THE DRAWINGS

FIG. 1A illustrates an exemplary process to perform virtual treatment using one or more dental appliances.

FIG. 1B shows an exemplary process for substituting dental appliances.

FIG. 2 shows two different appliances, in this case brackets, in their own virtual spaces.

FIG. 3 shows the brackets of FIG. 2, isometrically displayed in the same virtual space.

DESCRIPTION

Figure 4:
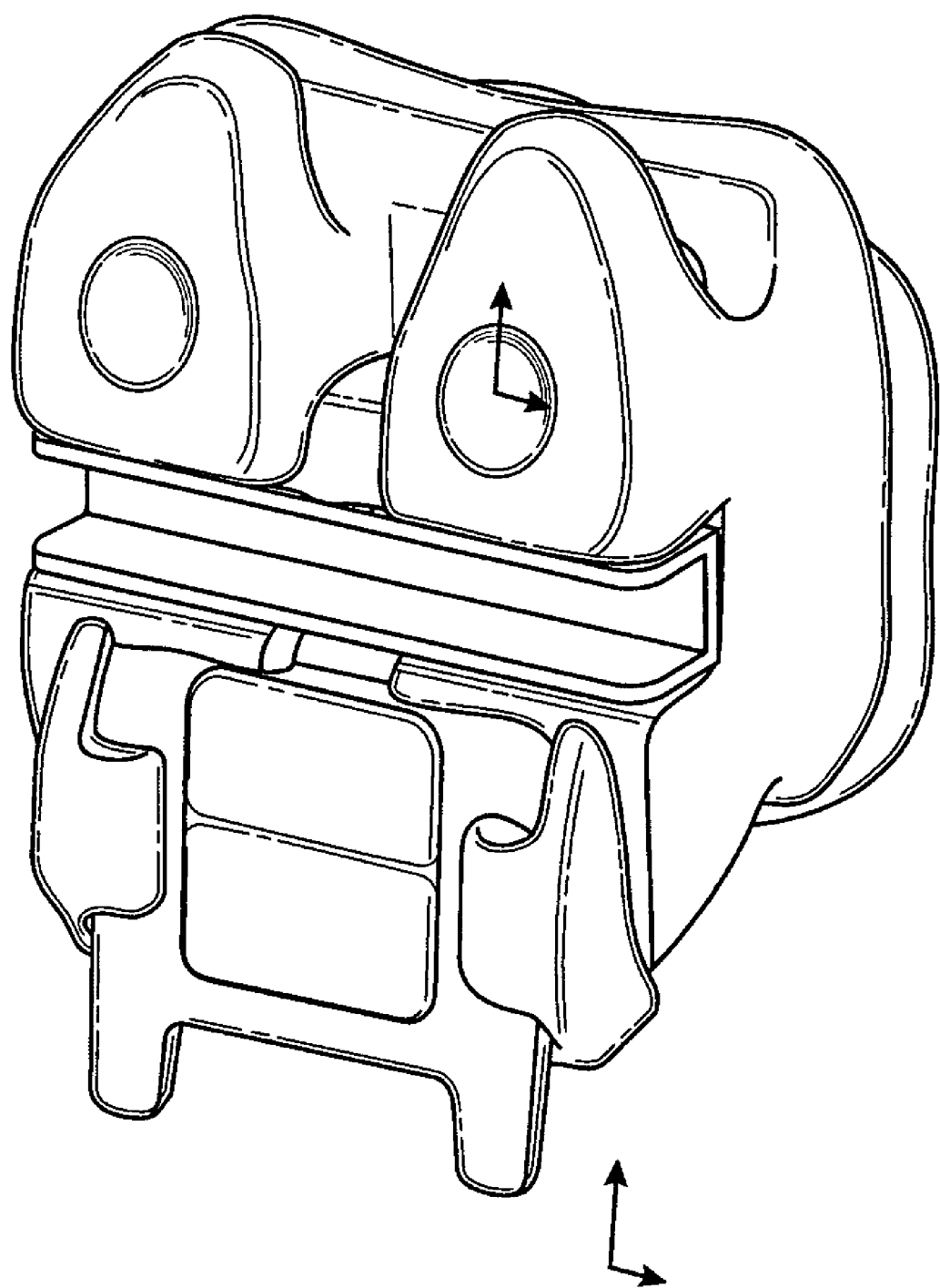
FIG. 4 shows the substitution based on an alignment of the brackets' dimensions or features.

FIG. 1A illustrates an exemplary process to perform virtual treatment using one or more dental appliances. The process includes receiving a digital model of a dental appliance (110); selecting a standard position and orientation (120); and mapping the digital model of the dental appliance to the standard position and orientation (130).

In one embodiment, the appliance can be a bracket. The digital model of the bracket can be received from a scanner or digitizer. There are several means of digitizing the brackets, among them computer tomography, acoustic imaging, surface tracing, and destructive scanning. Any of these could be direct or indirect. The former digitizes the body itself. The latter digitizes an impression or a mold of the body. The data set produced by the 3D acquisition system may, of course, be converted to other formats to be compatible with the software which is used for manipulating 3D images within the data set. Additionally, a variety of range acquisition systems, generally categorized by whether the process of acquisition requires contact with the three dimensional object, can be used. A contact-type range acquisition system utilizes a probe, having multiple degrees of translational and/or rotational freedom. By recording the physical displacement of the probe as it is drawn across the sample surface, a computer-readable representation of the sample object is made. A non-contact-type range acquisition device can be either a reflective-type or transmissive-type system. There are a variety of reflective systems in use. Some of these reflective systems utilize non-optical incident energy sources such as microwave radar or sonar. Others utilize optical energy. Those non-contact-type systems working by reflected optical energy further contain special instrumentation configured to permit certain measuring techniques to be performed (e.g., imaging radar, triangulation and interferometry). Optical, reflective, non-contact-type scanners and other non-contact-type scanners are preferred because they are inherently nondestructive (i.e., do not damage the sample object), are generally characterized by a higher capture resolution and scan a sample in a relatively short period of time. Next, a standard position and orientation is selected and the digital model of the dental appliance is mapped to the selected standard position and orientation.

A first embodiment to map appliances to the standard orientation and position is discussed next. When the physical brackets are digitized, they are held in the same position and orientation by a jig that allows them to be held in the same spatial location. In one embodiment, the bracket's slot can be used to attain the same location for models within a manufacturer's line as well as across manufacturers' lines because it is one of the most consistent geometric features with the greatest dimensional similarity among all brackets.

A second embodiment to map appliances to the standard orientations and positions is discussed below. This embodiment may be used independently of or in conjunction with the first embodiment discussed above. In this embodiment, the digital representations of the brackets are opened in software that can read the file format(s)—it is not required that the bracket representations are in the same format. For instance, one could be an STL and another can be an IGES, STEP, or CAD native (e.g. Pro/E, SolidWorks, etc.) file. Next, two or more files are loaded into the same software space at one time. Alternatively, each representation is loaded into its own space and these, in turn, are loaded to a common space. One of the files is selected as the base bracket to determine orientations and positions, or a separate object or coordinate system is selected as the basis to determine bracket orientations and positions. Any other bracket in the software space is aligned on the base bracket or the basis using known or common dimensions and features. Examples of common dimensions and features: within some amount of tolerance, all manufacturers' bracket slots are either 0.018" (0.46 mm) or 0.022" (0.56 mm) in the occlusogingival direction, the slot lengths are typically specified so the midpoint is easily determined, and the 'slot point' and 'base point' can be identified from these two. Any other bracket is saved independently with its newly-defined position and orientation.

In the case of contralateral brackets, the steps above could be followed or a bracket can simply be mirrored relative to a reference plane or surface to create its contralateral.

If the manufacturers' digital representations are available, the process is essentially the same as discussed above, except there is no need to digitize physical models. The positioning and orienting is less complex because all referents will be defined in the digital representations.

FIG. 1B shows an exemplary process for substituting dental appliances. First, an operator selects a model of a dental appliance previously placed on a tooth model (150). Next, the operator selects a model of a substitute dental appliance (160). The substitution can be based on a number of factors including fit, height of the appliance, comfort of the patient, or appearance of the appliance, among others. Based on the selection of the original model of the dental appliance and a substitute model of the appliance, the process of FIG. 1B places the substitute model in place of the original model of the dental appliance based on the standard position and orientation (170)

FIG. 2 shows two different brackets in their own virtual spaces. Their coordinate systems are different—not co-located as also can be seen by the difference in arrow orientations shown in the bottom left corner of each panel.

FIG. 3 shows the same two brackets isometrically displayed in the same virtual space. The coordinate system of the space does not coincide with that of either bracket. It can be seen that if one bracket were to replace the other, that the orientations, at least, would differ.

FIG. 4 shows that an alignment of the dimensions and/or features of the brackets causes them to have shared positions and orientations. If one is replaced with the other, these would not be changed in a virtual orthodontic setup.

The system can also be used to model the effects of more traditional appliances such as retainers, aligners and other removable dental appliances and therefore be used to generate optimal designs and treatment programs for particular patients.

The model of the brackets can be displayed and manually positioned or manipulated using a suitable dental CAD system. In this embodiment, a bracket is positioned on a tooth based on a prescription. Should the user wish to use a different bracket, the user merely selects a different bracket and indicates to the computer that the new bracket is to be used. The system deletes the first bracket and inserts the new bracket in the same spatial position and orientation of the original bracket without requiring the user to manually place the new bracket at the same location of the original bracket.

Alternatively, the system can automatically place the brackets for the user. In either a manual or automated placement system, the common coordinate system allows the user to select a substitute bracket and automatically insert the substitute bracket in place of the original bracket. A general flow of an exemplary process for defining and generating repositioning appliances for orthodontic treatment of a patient is discussed next. The process includes the methods, and is suitable for the apparatus, of the present invention, as will be described. The computational steps of the process are advantageously implemented as computer program modules for execution on one or more conventional digital computers.

As an initial step, a mold or a scan of a patient's teeth or mouth tissue is acquired. This generally involves taking casts of the patient's teeth and gums, and may also involve taking wax bites, direct contact scanning, x-ray imaging, tomographic imaging, sonographic imaging, and other techniques for obtaining information about the position and structure of the teeth, jaws, gums and other orthodontically relevant tissue. From the data so obtained, a digital data set is derived that represents the initial (that is, pretreatment) arrangement of the patient's teeth and other tissues.

The initial digital data set, which may include both raw data from scanning operations and data representing surface models derived from the raw data, is processed to segment the teeth into individual tooth models for manipulation. Digital models of each tooth can be produced, including measured or extrapolated hidden surfaces and root structures.

The desired final position of the teeth—that is, the desired and intended end result of orthodontic treatment—can be received from a clinician in the form of a prescription, can be calculated from basic orthodontic principles, or can be extrapolated computationally from a clinical prescription. With a specification of the desired final positions of the teeth and digital representations of the teeth themselves, the final position and surface geometry of each tooth can be specified to form a complete model of the teeth at the desired treatment end. Generally, in this step, the position of every tooth is specified. The result of this step is a set of digital data structures that represents an orthodontically correct repositioning of the modeled teeth relative to presumed-stable tissue. The teeth and tissue are both represented as digital data.

Having both a beginning position and a final position for each tooth, the process next defines a tooth path for the motion of each tooth. The tooth paths are optimized in the aggregate so that the teeth are moved in the quickest fashion with the least amount of round-tripping to bring the teeth from their initial positions to their desired final positions. (Round-tripping is any motion of a tooth in any direction other than directly toward the desired final position. Round-tripping is sometimes necessary to allow teeth to move past each other.) The tooth paths are segmented. The segments are calculated so that each tooth's motion within a segment stays within threshold limits of linear and rotational translation. In this way, the end points of each path segment can constitute a clinically viable repositioning, and the aggregate of segment end points constitute a clinically viable sequence of tooth positions, so that moving from one point to the next in the sequence does not result in a collision of teeth.

The threshold limits of linear and rotational translation are initialized, in one implementation, with default values based on the nature of the appliance to be used. More individually tailored limit values can be calculated using patient-specific data. The limit values can also be updated based on the result of an appliance-calculation, which may determine that at one or more points along one or more tooth paths, the forces that can be generated by the appliance on the then-existing configuration of teeth and tissue is incapable of effecting the repositioning that is represented by one or more tooth path segments. With this information, the subprocess defining segmented paths can recalculate the paths or the affected subpaths.

At various stages of the process, and in particular after the segmented paths have been defined, the process can, and generally will, interact with a clinician responsible for the treatment of the patient. Clinician interaction can be implemented using a client process programmed to receive tooth positions and models, as well as path information from a server computer or process in which other processes are implemented. The client process is advantageously programmed to allow the clinician to display an animation of the positions and paths and to allow the clinician to reset the final positions of one or more of the teeth and to specify constraints to be applied to the segmented paths. If the clinician makes any such changes, the subprocess of defining segmented paths is performed again.

The data processing aspects of the invention can be implemented in digital electronic circuitry, or in computer hardware, firmware, software, or in combinations of them. Data processing apparatus of the invention can be implemented in a computer program product tangibly embodied in a machine-readable storage device for execution by a programmable processor; and data processing method steps of the invention can be performed by a programmable processor executing a program of instructions to perform functions of the invention by operating on input data and generating output. The data processing aspects of the invention can be implemented advantageously in one or more computer programs that are executable on a programmable system including at least one programmable processor coupled to receive data and instructions from and to transmit data and instructions to a data storage system, at least one input device, and at least one output device. Each computer program can be implemented in a high-level procedural or object-oriented programming language, or in assembly or machine language, if desired; and, in any case, the language can be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of nonvolatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

To provide for interaction with a user, the invention can be implemented using a computer system having a display device such as a monitor or LCD (liquid crystal display) screen for displaying information to the user and input devices by which the user can provide input to the computer system such as a keyboard, a two-dimensional pointing device such as a mouse or a trackball, or a three-dimensional pointing device such as a data glove or a gyroscopic mouse. The computer system can be programmed to provide a graphical user interface through which computer programs interact with users. The computer system can be programmed to provide a virtual reality, three-dimensional display interface.

The invention has been described in terms of particular embodiments. Other embodiments are within the scope of the following claims. For example, the operations of the invention can be performed in a different order and still achieve desirable results.

What is claimed is:

1. A method for performing virtual treatment using one or more dental appliances, comprising:
   receiving a digital model of a dental appliance;
   selecting a standard position and orientation for the dental appliance in relation to a tooth model; and
   mapping the digital model of the dental appliance to the standard position and orientation, wherein the mapping comprises setting a plurality of digital models to the standard position and orientation;
   wherein the mapping comprises automatically placing a second dental appliance at a same position as a first dental appliance.

2. The method of claim 1, comprising placing a digital model of a first dental appliance on the tooth model.

3. The method of claim 2, comprising interchanging the first dental appliance with a second dental appliance.

4. The method of claim 1, comprising scanning a dental appliance to create the digital model.

5. The method of claim 1, comprising selecting a base object to determine the standard position and orientation.

6. The method of claim 5, wherein the base object is one of the dental appliances.

7. The method of claim 5, wherein the base object is a separate object.

8. The method of claim 1, comprising selecting a coordinate system as the basis for the standard position and orientation.

9. The method of claim 1, wherein the standard position and orientation is determined using predetermined dimensions and features on the dental appliances.

10. A method for performing virtual treatment using one or more dental appliances, comprising:
    receiving a digital model of a dental appliance;
    selecting a standard position and orientation for the dental appliance in relation to a tooth model; and
    mapping the digital model of the dental appliance to the standard position and orientation;
    wherein the standard position and orientation is determined using predetermined dimensions and features on the dental appliances;
    wherein one feature is an appliance slot.

11. The method of claim 10, wherein the slot comprises an 0.018" (0.46 mm) or 0.022" (0.56 mm) width channel running in a mesiodistal direction.

12. The method of claim 10, wherein one dimension comprises a slot length.

13. The method of claim 10, wherein one dimension comprises a slot point.

14. The method of claim 10, wherein one dimension comprises a base point.

15. A method for performing virtual treatment using one or more dental appliances, comprising:
    receiving a digital model of a dental appliance;
    selecting a standard position and orientation for the dental appliance in relation to a tooth model; and
    mapping the digital model of the dental appliance to the standard position and orientation;
    wherein the dental appliance is a bracket;

wherein the bracket is a contralateral bracket, comprising mirroring the bracket relative to a reference plane or surface to create a contralateral model.

16. A method for performing virtual treatment using one or more dental appliances, comprising:
   receiving a digital model of a dental appliance;
   selecting a standard position and orientation for the dental appliance in relation to a tooth model;
   mapping the digital model of the dental appliance to the standard position and orientation; and
   interchanging the dental appliances in accordance with specified criteria;
   wherein one criteria includes one of: a best fit on the tooth, a material fit, an obtrusiveness measure, and a cost.

17. A method for performing; virtual treatment using one or more dental appliances, comprising;
   receiving a digital model of a dental appliance;
   selecting a standard position and orientation for the dental appliance in relation to a tooth model;
   mapping the digital model of the dental appliance to the standard position and orientation; and
   generating a template to place the dental appliance on a tooth;
   wherein the appliance is a bracket, comprising fabricating a wire based on the bracket's position and orientation.

18. A method for use in virtual treatment of teeth using appliances, comprising:
   providing a digital model of each of a plurality of different brackets; and
   mapping the digital models of the different brackets based on at least one common feature element of each bracket so that each of the digital models of the different brackets, once positioned in relation to a digital representation of a tooth or orthodontic appliance, can be respectively replaced, by reference to the common feature element, by a different digital model that will be positioned in the same spatial position and orientation as the original digital model.

19. The method of claim 18, wherein:
   the digital models are mapped based on at least one common feature element of each bracket and an orientation in a three-dimensional coordinate system.

20. The method of claim 19, wherein:
   the digital model is replaced by reference to the common feature element and the orientation of the brackets in the three-dimensional coordinate system.

21. A method for use in virtual treatment of teeth using appliances, comprising:
   providing a digital model of each of a plurality of different brackets;
   mapping the digital models of the different brackets based on at least one common feature element of each bracket;
   digitally placing a first one of the digital models in conjunction with a digital representation of a tooth or an orthodontic appliance; and
   replacing the first digital model with a second digital model.

22. The method of claim 21, wherein:
   the replacing step comprises placing the second digital model by reference to the at least one common feature element of each bracket so that the second digital model is positioned in the same spatial position and orientation of the first digital model in relation to the digital representation of the tooth or orthodontic appliance.

23. The method of claim 22, wherein:
   the replacing step comprises placing the second digital model by reference to the at least one common feature element of each bracket so that the second digital model is positioned in the same spatial position and orientation of the first digital model in relation to the digital representation of the tooth or orthodontic appliance and an orientation in a three-dimensional coordinate system.

* * * * *